United States Patent [19]
Behl et al.

[11] Patent Number: 4,760,059
[45] Date of Patent: Jul. 26, 1988

[54] RECTAL DOSAGE FORM

[75] Inventors: Charanjit Behl, Bloomfield; Joel Unowsky, Livingston, both of N.J.

[73] Assignee: Hoffmann-La Roche Inc., Nutley, N.J.

[21] Appl. No.: 762,248

[22] Filed: Aug. 5, 1985

[51] Int. Cl.$^4$ ............... A61K 9/02; A61K 47/00
[52] U.S. Cl. ............... 514/206; 424/DIG. 15; 514/198; 514/199; 514/200; 514/965; 514/966; 514/970
[58] Field of Search ............... 424/DIG. 15; 514/786, 514/206, 965, 966, 970, 198, 199, 200

[56] References Cited

U.S. PATENT DOCUMENTS

| 4,156,719 | 5/1979 | Sezaki et al. | 424/118 |
| 4,406,896 | 9/1983 | Higuchi et al. | 514/161 |
| 4,525,339 | 6/1985 | Behl et al. | 424/16 |
| 4,579,730 | 4/1986 | Kidron et al. | 424/19 |

FOREIGN PATENT DOCUMENTS

| 55-62007 | 5/1980 | Japan . |
| 57-64610 | 4/1982 | Japan . |
| 57-158719 | 9/1982 | Japan . |
| 1563311 | 3/1980 | United Kingdom . |
| 1601613 | 11/1981 | United Kingdom . |

OTHER PUBLICATIONS

Fuller C.A. 103, #200886A (1985) of EP 152896 28 Aug. 1985, (Swiss 22 Feb. 1984), 22 pp.
Sekine C.A. 103, #189155p (1985) of J. Pharmacobio-Dyn 8(8): 653–660 (1985).
Sankyo C.A. 102, #154814e (1985) of JP 59227822, 21 Dec. 1984, 7 pp.
Murakami et al. GA 101, #48186w (1984) of Chem. Pharm. Bull. 32 (5): 1948–1955 (1984).
Yata C.A. 100, #26030t (1984) of EP 91502, 19 Oct. 1983, 38 pp.
Higuchi et al. C.A. 100, #12654n (1984) of U.S. 4406896, 27 Sep. 1983, 12 pp.
Toyojozo C.A. 97, #150726h (1982) of JP 82 99519, 21 Jun. 1982, 5 pp.
Kawamura et al. C.A. 87, #189465r (1977) of Japan Kokai 77 83923, 13 Jul. 1977, 4 pp.

*Primary Examiner*—Shep K. Rose
*Attorney, Agent, or Firm*—Jon S. Saxe; Bernard S. Leon; Richard J. Mazza

[57] ABSTRACT

The rectal absorption of the beta-lactam antibiotic ceftriaxone in a solid dosage form is enhanced with chenodeoxycholic acid or its sodium salt, in the presence of a carrier consisting of a mixture of two or more glycerides of $C_{12}$ to $C_{18}$ fatty acids.

7 Claims, No Drawings

RECTAL DOSAGE FORM

BACKGROUND OF THE INVENTION

The use of suppositories to deliver beta-lactam antibiotics which are orally inactive is known. Such suppositories are ordinarily composed of the antibiotic, a base substance such as WITEPSOLS, e.g. WITEPSOL H-15, which are a mixture of higher chain ($C_{12}$–$C_{18}$) fatty acid glycerides, and a substance to promote absorption of the antibiotic in the rectum. Such substances, such as, probenacid and fatty acids of $C_8$ to $C_{14}$ chain length have been used in the past to promote absorbability of antibiotics in suppository form. See, for example, Japanese Application No. 20590 - J5-2105-220 and U.S. Pat. No. 4,38,306 respectively. Furthermore, the use of mixtures of fatty acid glycerides of $C_2$–$C_{12}$ chain length as enhancers has also been disclosed, see, for example, Swiss Application No. 858/84.

DESCRIPTION OF THE INVENTION

The present invention relates to a rectal dosage form which contains as its active ingredient, a beta-lactam antibiotic, a base/vehicle and an enhancer which provides pharmacologically active amounts of the antibiotic in the blood.

As suitable beta-lactam antibiotics there may be mentioned antibiotics known in the art which have as their central ring system the beta-lactam ring, e.g., compounds of the formula

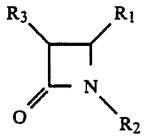

wherein $R_1$ is hydrogen or optionally substituted alkyl, $R_2$ is $SO_3^-M^+$ is a proton or cation, $R_3$ is an acylamino group of hydroxyalkyl or $R_1$ and $R_2$ together with the beta-lactam (acetidinone) ring to which they are bonded represent

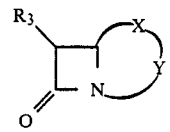

wherein X represents S, O, SO, $SO_2$ or $CH_3$ and y represents the group

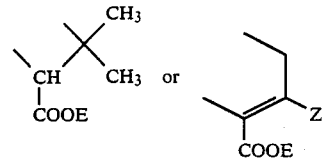

in which the carbon atom which carries the —COOE group is bonded to the nitrogen atom of the beta-lactam ring, Z represents hydrogen, halogen, alkoxy or $CH_2$-T, T denotes hydrogen, alkyl —CO—O—, pyridinium, carboramidopyridinium, aminopyridinium, carbamoyloxy, azido, cyano, hydroxyl, the group -S-phenyl which can be substituted or the group -S-het wherein het represents an optionally substituted 5- or 6-membered heterocyclic ring and E represents hydrogen, a pharmaceutically usable ester group or salt-forming cation.

Especially preferred beta-lactam antibiotics and their pharmaceutically acceptable salt and esters and hydrates of these compounds include ceftriaxone, a cephalosporin disclosed and claimed in U.S. Pat. No. 4,327,210; carumonam, a monocyclic beta-lactam disclosed and claimed in European Patent No. EP73061; piperacillin, a penicillin disclosed and claimed in U.S. Pat. No. 4,112,090; cefamandole, a cephalosporin disclosed and claimed in U.S. Pat. No. 3,641,021; cefazolin, a cephalosporin disclosed and claimed in U.S. Pat. No. 3,516,997 and mezlocillin a penicillin disclosed and claimed in U.S. Pat. No. 3,974,142.

Bases/vehicles which are useful in the compounding of the rectal dosage form include the mixed glycerides of chain $C_{12}$ to $C_{18}$ fatty acids, preferably even numbered, such as, the WITEPSOL class of suppository bases. Examples of such WITEPSOLS are:

| WITEPSOL | MP melting point °C. open capillary | SP Solidification point °C. | IA Acid Value | IS Saponification value | II Iodine value | IOH Hydroxyl-value | USM Unsaponifiable matter |
| --- | --- | --- | --- | --- | --- | --- | --- |
| H 5   | 34,0–36,0 | 33,0–35,0 | 0,2 max. | 235–245 | 2 max. | 5 max.  | 0,3 max. |
| H 12  | 32,0–33,5 | 29,0–33,0 | 0,2 max. | 240–255 | 3 max. | 15 max. | 0,3 max. |
| H 15  | 33,5–35,5 | 32,5–34,5 | 0,2 max. | 230–240 | 3 max. | 15 max. | 0,3 max. |
| H 175 | 34,5–36,5 | 32,0–34,0 | 0,7 max. | 225–245 | 3 max. | 15 max. | 1,0 max. |
| H 185 | 38,0–39,0 | 34,0–37,0 | 0,2 max. | 220–235 | 3 max. | 15 max. | 0,3 max. |
| H 19  | 33,5–35,5 | 32,0–35,0 | 0,2 max. | 230–240 | 7 max. | 20–30   | 0,3 max. |
| H 32  | 31,0–33,0 | 30,0–32,5 | 0,2 max. | 240–250 | 3 max. | 3 max.  | 0,3 max. |
| H 35  | 33,5–35,5 | 32,0–35,0 | 0,2 max. | 240–250 | 3 max. | 3 max.  | 0,3 max. |
| H 37  | 36,0–38,0 | 35,0–37,0 | 0,2 max. | 225–245 | 3 max. | 3 max.  | 0,3 max. |
| H 39  | 38,0–40,0 | 37,0–39,5 | 0,2 max. | 220–240 | 3 max. | 3 max.  | 0,3 max. |
| H 42  | 41,0–43,0 | 40,0–42,5 | 0,2 max. | 220–240 | 3 max. | 3 max.  | 0,3 max. |
| W 25  | 33,5–35,5 | 29,0–33,0 | 0,3 max. | 225–240 | 3 max. | 20–30   | 0,3 max. |
| W 31  | 35,0–37,0 | 30,0–33,0 | 0,3 max. | 225–240 | 3 max. | 25–35   | 0,5 max. |
| W 35  | 33,5–35,5 | 27,0–32,0 | 0,3 max. | 225–235 | 3 max. | 40–50   | 0,3 max. |
| W 45  | 33,5–35,5 | 29,0–34,0 | 0,3 max. | 225–235 | 3 max. | 40–50   | 0,3 max. |
| S 55  | 33,5–35,5 | 28,0–33,0 | 1,0 max. | 215–230 | 3 max. | 50–65   | 2,0 max. |
| S 58  | 32,0–33,5 | 27,0–29,0 | 1,0 max. | 215–225 | 7 max. | 60–70   | 2,0 max. |
| E 75  | 37,0–39,0 | 32,0–36,0 | 1,3 max. | 220–230 | 3 max. | 15 max. | 3,0 max. |
| E 76  | 37,0–39,0 | 31,0–35,0 | 0,3 max. | 220–230 | 3 max. | 30–40   | 0,5 max. |

-continued

| WITEPSOL | MP melting point °C. open capillary | SP Solidification point °C. | IA Acid Value | IS Saponification value | II Iodine value | IOH Hydroxyl-value | USM Unsaponifiable matter |
| --- | --- | --- | --- | --- | --- | --- | --- |
| E 85 | 42,0–44,0 | 37,0–42,0 | 0,3 max. | 220–230 | 3 max. | 15 max. | 0,5 max. |

The enhancer utilized to promote rectal absorption is chenodeoxycholic acid, or its sodium salt.

The rectal dosage form in accordance with the invention preferably contian from about 25 mg to about 2000 mg of active substance, e.g., ceftriaxone, cefamondole, mezlocillin, cefazolin, piperacillin or carumonam, especially from about 50 mg to about 500 mg.

The active substance: Base/vehicle ratio in the suppository in accordance with the invention conveniently varies between about 3:1 and about 1:20 and preferably lies between about 1:1 and about 1:3. The active substance:enhancer ratio conveniently lies between about 1:2 and about 24:1 preferably between about 2:1 and about 8:1.

The pharmaceutical composition for rectal administration in accordance with this invention is generally used as a rectal suppository or a preparation prepared by dispersing the pharmacologically-active substance, the chenodeoxycholic acid or its sodium salt and the Witepsol and other ingredients in a liquid oleaginous base to prepare a fluid preparation e.g. suspension, ointment, gel, cream, etc. and by filling this preparation in soft gelatin capsules or syringe or tubes, e.g. as an enema.

The rectal dosage forms in accordance with the invention can also contain adjuvants which are known per se for the purpose of achieving a desired consistency. Further, they can contain water-soluble carriers such as polyethylene glycol, polypropylene glycol, glycerogelatine, methylcellulose or carboxymethylcellulose. There also come into consideration wetting agents, e.g. non-ionic wetting agents such as polyoxyethylene sorbitan fatty acid esters, polyoxyethylene sorbitol fatty acid esters, polyoxyethylene fatty acid esters, glycerine fatty acid esters, e.g. mixtures of mono; di- or triglycerides of fatty acids as well as higher alcohol esters of polyoxyethylene, or anionic wetting agents such as esters of lower alkylsulphonic acids or cationic surfactants. Further, the rectal dosage forms can contain suitable emulsifying and dispersing agents, agents for adjusting the viscosity and coloring substances.

These dosage forms can be manufactured in accordance with the invention by melting the base/vehicle together with the enhancer by warming, homogeneously dispersing the active substance and, if desired, customary therapeutically inert adjuvants for rectal dosage forms in the melt obtained and formulating the dispersion obtained into suppositories, capsules, or other rectal delivery system.

In order to demonstrate the high bioavailability levels of active substance when incorporated in a rectal dosage form, e.g. as a suppository it was formulated in the following compositions:

| | | |
| --- | --- | --- |
| Ceftriaxone disodium salt trihydrate [corresponding to 502.2 mg of ceftriaxone (83.7% active)] | 600 mg | 600 mg |
| WITEPSOL H-15 | 2675 mg | 1275 mg |
| Chenodeoxycholic acid, sodium salt | 125 mg | 125 mg |

-continued

| | | |
| --- | --- | --- |
| | 3400 mg | 2000 mg |

The bioavailability of the ceftriaxone was computed and demonstrated as follows utilizing an intravenous dosage as a standard in the baboon model:

1. Intravenous Administration

The baboons were sedated with ketone hydrochloride (5–10 mg/Kg) administered intramuscularly. Then a zero time blood sample was withdrawn followed by injection of one ml of ceftriaxone solution into the superior saphenous vein on the back of the leg, using a one ml disposable tuberculin syringe and a 26 gauge needle.

2. Rectal Administration

The baboons were fasted 24 hours prior to the administration of the drug. Using a glass rod, the above suppository was pushed into the rectum. The rectal orifice was taped for about 20 minutes to prevent expulsion of the suppository or leakage of the formulation.

3. Determination of Plasma Concentrations of Ceftriaxone

Blood samples were withdrawn at zero time (prior to drug administration) 5, 30, 60, 120, 240, 360, 480, 600, 720 and 1440 minutes following intravenous dosing. Zero hour blood samples were withdrawn prior to rectal dosing. After rectal dosing, blood samples were obtained at 0, 5, 30, 60, 120, 240, 360, 480, 600, 720 and 1440 minutes. The blood was withdraw from veins in the femoral region with a heparinized 3 ml syringe fitted with a 22 gauge needle. One ml of blood was placed into heparinized 1.5 ml Eppendorf centrifuge tubes an centrifuged for 30 seconds in an Eppendorf centrifuge. The plasma was withdrrawn and frozen at $-20°$ C. until bioassayed for ceftriazone concentration.

4. Bioassay

The plasma samples were deproteinized with acetonitrile and antibiotic levels were determined by bioassay on a Nunc plate. E. coli 1346 grown overnight on an antibiotic agar #1 slant was washed with saline to give a suspension with 90% transmittance on a Bausch and Lomb Spectronic 20 (650 NM). Sixteen ml of this suspension was added to 600 ml of molten antibiotic agar #1. Two hundred ml of the seeded agar was poured into each Nunc plate ($243 \times 243 \times 18$ mm). Agar wells were punched and removed from the agar plate so that 20 mcl of the sample or standard drug could be added to each well according to the semi Qausi Latin square.

5. Data Analysis

Plasma concentrations were plotted as a function of time for both the rectal and the intravenous data. The areas under the curves (AUC) were calculated and the adjusted percent bioavailabilities were computed from the following equation:

$$\frac{(AUC\ \text{Rectal})}{(AUC\ \text{Intravenous})} \times \frac{(\text{Dose Intravenous})}{(\text{Dose Rectal})} \times 100$$

The results obtained for the above suppository which represents a 4:1 ratio of active substance to enhancer is as follows:

| Time (minutes) | Baboon #1 ($\mu$g/ml) | Baboon #2 ($\mu$g/ml) | Baboon #3 ($\mu$g/ml) | Baboon #4 ($\mu$g/ml) |
|---|---|---|---|---|
| 0 | N.D. | N.D. | N.D. | N.D. |
| 5 | 2.8 | 1.6 | 1.9 | 4.2 |
| 30 | 34.3 | 34 | 16.2 | 41.5 |
| 60 | 45.8 | 48 | 97.6 | 83.2 |
| 120 | 51.2 | 71.5 | 57.8 | 65.8 |
| 240 | 43.4 | 37.6 | 37.8 | 48.8 |
| 360 | 37.5 | 31.5 | 20.9 | 28.8 |
| 480 | 38.2 | 32.4 | 16.4 | 14.9 |
| 600 | 31.3 | 28.3 | 12.8 | 11.1 |
| 720 | 22.1 | 10.1 | 10.9 | 6.2 |
| 1440 | 5.6 | 1.8 | 2.6 | 0.7[1] |

Average Peak Plasma Level ($C_{max}$) = 75.9 $\mu$g/ml
Standard Deviation = ±19.6
[1] Values were below standard curve but were used for calculations.

| Baboon # | AUC (480 min) | Dose(mg/kg) | % Bioavailability (480 min) = $\frac{[\text{AUC Rectal}]}{[\text{AUC IV}]} \times \frac{[\text{Dose IV}]}{[\text{Dose Rectal}]} \times 100$ |
|---|---|---|---|
| #1 | 327.6 | 21.7 | 73 |
| #2 | 329.9 | 19.6 | 65 |
| #3 | 301.6 | 28.6 | 61 |
| #4 | 351.3 | 21.7 | 75 |

$\overline{X}$ % Bioavailability = 68.5
Standard Deviation = 6.6

Following the above procedures and utilizing similar formulations for the compounds carumanam, piperacillin, cefamondole, cefazolin or mezlocillin the following results were obtained:

| carumonam | |
|---|---|
| average Peak Plasma Level ($C_{max}$) = $\overline{X}$ % Bioavailability = piperacillin | 5.6 $\mu$g/ml<br>47.0 |
| average Peak Plasma Level ($C_{max}$) = $\overline{X}$ % Bioavailability = cefamandole | 1.2 $\mu$g/ml<br>27.0 |
| Average Peak Plasma Level ($C_{max}$) = $\overline{X}$ % Bioavailability = cefazolin | 22 $\mu$g/ml<br>100.0 |
| Average Peak Plasma Level ($C_{max}$) = $\overline{X}$ % Bioavailability = mezlocillin | 42 $\mu$g/ml<br>55 |
| Average Peak Plasma Level ($C_{max}$) = $\overline{X}$ % Bioavailability = | 3 $\mu$g/ml<br>43 |

It should be noted that the low $C_{max}$ levels for carumonam, mezlocillin and piperacillin represent longer sustained levels which contribute to increased bioavailability although at low levels of $C_{max}$.

What is claimed:

1. A solid rectal dosage form comprising a therapeutically effective amount of ceftriaxone or a pharmaceutically acceptable salt thereof, chenodeoxycholic acid or its sodium salt in an amount sufficient to enhance the rectal absorption of the ceftriaxone or salt thereof, and a carrier for the foregoing consisting of a mixture of two or more glycerides of $C_{12}$-$C_{18}$ fatty acids.

2. The solid rectal dosage form of claim 1 wherein the ratio of ceftriaxone or salt thereof to carrier is from about 3:1 to about 1:20.

3. The solid rectal dosage form of claim 2 wherein the ratio of ceftriaxone or salt thereof to carrier is from about 1:1 to about 1:3.

4. The solid rectal dosage form of claim 1 wherien the ratio of ceftriaxone of salt thereof to chenodeoxycholic acid or its sodium salt is form about 1:2 to about 24:1.

5. The solid rectal dosage form of claim 1 wherein the ratio of ceftriaxone or salt thereof to chenodeoxycholic acid or its sodium salt is from about 2:1 to about 8:1.

6. The solid rectal dosage from of claim 1 wherein the ratio of ceftriaxone or salt thereof to carrier is about 1:2.

7. The solid rectal dosage form of claim 1 wherein the ratio of ceftriaxone or salt thereof to chenodeoxycholic acid or its sodium salt is about 4:1.

* * * * *

UNITED STATES PATENT AND TRADEMARK OFFICE
CERTIFICATE OF CORRECTION

PATENT NO. : 4,760,059
DATED : July 26, 1988
INVENTOR(S) : CHARANJIT BEHL AND JOEL UNOWSKY It is certified that error appears in the above-identified patent and that said Letters Patent is hereby corrected as shown below:

In column 6, on line 34, the word "wherien" should be -- wherein --;

In column 6, on line 35, the word "of" second occurrence should be -- or --; and In column 6, on line 36, the word "form" should be -- from --.

Signed and Sealed this

Twenty-eighth Day of November 1989

Attest:

JEFFREY M. SAMUELS

Attesting Officer     Acting Commissioner of Patents and Trademarks